(12) United States Patent
Diehl et al.

(10) Patent No.: US 11,534,564 B2
(45) Date of Patent: Dec. 27, 2022

(54) BREATHING APPARATUS COMPRISING A DIFFERENTIAL PRESSURE SENSOR

(71) Applicant: WEINMANN EMERGENCY MEDICAL TECHNOLOGY GMBH & CO. KG, Hamburg (DE)

(72) Inventors: Marcus Diehl, Hamburg (DE); Stefan Hein, Hamburg (DE); Matthias Pulla, Hamburg (DE); Frank Herrmann, Armstedt (DE)

(73) Assignee: WEINMANN EMERGENCY MEDICAL TECHNOLOGY GMBH & CO. KG, Hamburg (DE)

( * ) Notice: Subject to any disclaimer, the term of this patent is extended or adjusted under 35 U.S.C. 154(b) by 550 days.

(21) Appl. No.: 16/485,537

(22) PCT Filed: Feb. 16, 2018

(86) PCT No.: PCT/DE2018/000042
§ 371 (c)(1),
(2) Date: Aug. 13, 2019

(87) PCT Pub. No.: WO2018/149435
PCT Pub. Date: Aug. 23, 2018

(65) Prior Publication Data
US 2020/0046920 A1    Feb. 13, 2020

(30) Foreign Application Priority Data
Feb. 20, 2017    (DE) .................... 10 2017 001 558.9

(51) Int. Cl.
*A61M 16/00* (2006.01)
*F04D 25/08* (2006.01)
*G01F 1/42* (2006.01)
*A61B 5/087* (2006.01)
*F04D 29/056* (2006.01)
(Continued)

(52) U.S. Cl.
CPC ......... *A61M 16/0066* (2013.01); *A61B 5/087* (2013.01); *A61M 16/0003* (2014.02);
(Continued)

(58) Field of Classification Search
CPC .......... A61M 16/0066; A61M 16/0003; A61M 2016/0027; A61M 2205/3334;
(Continued)

(56) References Cited

U.S. PATENT DOCUMENTS 4,403,514 A    9/1983  Osborn
4,859,858 A *  8/1989  Knodle ................ A61B 5/0836
                                                   250/504 R
(Continued)

FOREIGN PATENT DOCUMENTS

DE         10035938 A1    2/2001
DE      102014119146 A1   6/2016
(Continued)

*Primary Examiner* — Joseph D. Boecker
*Assistant Examiner* — Brian T Khong
(74) *Attorney, Agent, or Firm* — Lucas & Mercanti, LLP; Klaus P. Stoffel (57) ABSTRACT

A method and apparatus for breathing including a blower mounted in a specific part made of silicone, which reduces blower immissions and emissions. The conducting structure influences the flow of the respiratory gas in order to reduce interference when measuring the volumetric flow.

5 Claims, 5 Drawing Sheets

(51) Int. Cl.
*F04D 29/58* (2006.01)
*F04D 17/16* (2006.01)
*F04D 29/66* (2006.01)

(52) U.S. Cl.
CPC ........... *F04D 25/08* (2013.01); *F04D 29/056* (2013.01); *F04D 29/5826* (2013.01); *G01F 1/42* (2013.01); *A61M 2016/0027* (2013.01); *A61M 2205/3334* (2013.01); *A61M 2205/3372* (2013.01); *A61M 2205/42* (2013.01); *F04D 17/16* (2013.01); *F04D 29/668* (2013.01)

(58) Field of Classification Search
CPC ...... A61M 2205/3372; A61M 2205/42; A61M 16/006; A61B 5/087; F04D 25/08; F04D 29/056; F04D 29/5826; F04D 17/16; F04D 29/668; G01F 1/42; G01F 1/34
See application file for complete search history.

(56) References Cited

U.S. PATENT DOCUMENTS

| | | | | |
|---|---|---|---|---|
| 5,347,843 | A | * | 9/1994 | Orr .......................... G01F 1/363 600/538 |
| 5,379,650 | A | * | 1/1995 | Kofoed .................. G01F 1/363 73/861.52 |
| 5,535,633 | A | * | 7/1996 | Kofoed .................. A61B 5/087 73/861.52 |
| 6,912,919 | B2 | * | 7/2005 | Shiba ........................ G01F 1/40 73/861.52 |
| 2008/0092898 | A1 | | 4/2008 | Schneider |

FOREIGN PATENT DOCUMENTS

| | | | | |
|---|---|---|---|---|
| EP | 0331772 | A1 | | 9/1989 |
| EP | 552916 | A1 | * | 7/1993 ............. A61B 5/087 |
| EP | 0552916 | A1 | | 7/1993 |

\* cited by examiner

BREATHING APPARATUS COMPRISING A DIFFERENTIAL PRESSURE SENSOR

CROSS-REFERENCE TO RELATED APPLICATIONS

The present application is a 371 of International application PCT/DE2018/000042, filed Feb. 16, 2018, which claims priority of DE 10 2017 001 558.9, filed Feb. 20, 2017, the priority of these applications is hereby claimed and these applications are incorporated herein by reference.

BACKGROUND OF THE INVENTION

The invention relates to a ventilator apparatus and a ventilation method. In particular, an application in mobile emergency ventilators is considered.

In the case of insufficient respiration, or the lack of independent respiration, of a living being requiring oxygen, the respiratory work, as a life-saving measure, must be carried out by a third party, either manually, for example by mouth-to-mouth ventilation or with the aid of ventilation bags, or by a machine with a ventilator in order to ensure gas exchange in the lung and in order thus to supply the organs with oxygen and exhale $CO_2$.

Machine ventilation, which, in the form of ventilators, is part of the medical equipment of first alders and clinical staff, is a reliable process according to the prior art.

By way of volume and/or pressure control, modern ventilators and ventilation methods offer important functions for effective and, at the same time, sparing ventilation of patients. Pressure that is too high can damage lung tissue while a ventilation volume that is too small has underprovision of oxygen as a consequence. Additionally, the ventilation frequency is precisely adaptable to international guidelines using known ventilators; this is intended to ensure effective ventilation, even in the case of resuscitation measures.

To have a reliable and accurate control of the volumetric flow rate and of the pressure of the ventilation using a ventilator, these parameters must be determined sufficiently accurately over their entire dynamic range. In relation to determining a volumetric flow rate present, a quadratic dependence arises in the case of a conventional measurement arrangement of a differential pressure measuring method within the meaning of a simple stop or a simple resistor, said quadratic dependence only producing small changes in the measurable differential pressure in the range of low volumetric flow rates, and hence meaning a poorer resolvability than at higher volumetric flow rates.

As a rule, the volumetric flow rate of the respiratory gas in a respiratory gas line in ventilators is determined with the aid of a differential pressure measuring apparatus, which has at least one differential pressure measurement path and a differential pressure sensor. Depending on the volumetric flow rate of the respiratory gas flowing through the differential pressure measurement path, the differential pressure measurement path produces a differential pressure at the measurement outputs, said differential pressure being captured by means of the differential pressure sensor and being digitized where necessary. Consequently, the volumetric flow rate/differential pressure characteristic of the differential pressure measuring apparatus is composed at least of the volumetric flow rate/differential pressure characteristic of the differential pressure measurement path and the characteristic of the differential pressure sensor.

SUMMARY OF THE INVENTION

It is an object of the invention to develop a ventilator apparatus having a differential pressure measuring apparatus which has an improved volumetric flow rate/differential pressure characteristic for determining the volumetric flow rate in a flow channel of a ventilator such that there is a better resolvability in the region of low volumetric flow rates.

According to the invention, this object is achieved by virtue of the ventilator apparatus having a differential pressure measuring apparatus, the differential pressure measurement path thereof facilitating the realization of an improved volumetric flow rate/differential pressure characteristic.

A ventilator apparatus according to the invention has a respiratory gas line, a respiratory gas being guidable therethrough to a patient. A pressure measurement path is integrated in the respiratory gas line in regions, said pressure measurement path being embodied as a differential pressure measurement path. In an advantageous embodiment of the invention, the pressure measurement path is integrated in an adapter that is insertable into the respiratory gas line.

In an advantageous embodiment of the invention, the adapter additionally has a positive pressure protection valve in addition to the differential pressure measurement path, the former rendering a quick pressure equalization realizable in the case of positive pressure in the respiratory gas line.

The differential pressure measurement path has a flow channel which has a substantially ring-shaped embodiment or embodiment as a ring segment in an advantageous embodiment of the invention and which has two measurement openings at its radially outer delimiting face. A measurement line with a pipe-like embodiment, which leads to a measurement output of the differential pressure measurement path and is integrated into a pressure measurement nozzle in each case, respectively adjoins the measurement openings. Furthermore, a sleeve-like and/or cylindrical hollow wall-type realization of the flow channel is also conceivable.

At least in the region of the measurement openings, the measurement lines have an essential component directed tangential to the outer delimiting face of the flow channel. Furthermore, the flow channel of the differential pressure measurement path has a smaller cross section than the connecting respiratory gas line in an advantageous embodiment of the invention.

A differential pressure measuring unit that converts the analog pressure values into digital measurement values and makes these evaluable with the aid of at least one differential pressure sensor or at least two simple pressure sensors and further electronic components, such as an analog-to-digital converter, for example, is connectable to the measurement outputs. Likewise, the use of a differential pressure measuring unit, which is realized as a differential pressure sensor with a digital interface for outputting the pressure measurement values, is considered according to the invention.

The measurement openings are arranged in the flow channel of the differential pressure measurement path in such a way that, in the case of a given flow direction, there is, on account of the wall friction between respiratory gas and flow channel occurring between the measurement openings, a lower static pressure drop at the first measurement output, arranged upstream of the second measurement output in the flow direction, than at the second measurement output that is arranged downstream of the first measurement output in the flow direction. As a result of the measurement lines having an essential tangential component in the region of the measurement openings, the cross section of the measurement openings is increased in comparison with the cross section of the measurement lines in the surface of the flow channel.

In an advantageous embodiment of the invention, the alignment of the measurement lines, at least in the region of the measurement opening on the flow channel, lies in an angle range from 0° to 60° as measured from the axis defined by the local tangent in the direction of an axis orthogonal thereto, which extends in the radial direction. Here, an angle of 0° corresponds to completely tangential alignment and an angle of 90° corresponds to completely radial alignment of the measurement line in relation to the radially outer lying delimiting face of the flow channel with the ring-shaped or ring segment-shaped embodiment. In a particularly advantageous embodiment of the invention, the alignment of the measurement line lies in an angle range of 0° to 45°, accordingly related to the axes specified above, at least in the region of the measurement openings on the flow channel.

Furthermore, the first measurement opening is arranged on the outer circumference of the flow channel in such a way that respiratory gas flowing through the flow channel drags along gas from there and hence produces a local negative pressure component at the first measurement output in a manner similar to the Venturi principle or a jet pump, said local negative pressure component being related to the flow speed of the respiratory gas. The second measurement opening is arranged on the outer circumference of the flow channel in such a way that the respiratory gas flowing through the flow channel is pressed therein and consequently produces a local positive pressure component at the second measurement output that depends on the flow speed. As a result of the dependence on the flow speed, the aforementioned negative and positive pressure components are defined as dynamic pressure components.

The local superposition of static and dynamic pressure leads to a change in the actual differential pressure that is measurable at the pickups. The measurable pressure decreases on the side of the higher static pressure and increases on the side of the lower static pressure.

The measurable pressure is the sum of the static pressure and the ram pressure at the respective measurement point:

$$p_{total} = p_{ram} + p_{stat}$$

On account of the different local superposition of static and dynamic pressure, the measurable differential pressure is less than the actual difference of the static pressures at the two measurement outputs:

$$p_{stat1} + p_{stat2} > p_{total1} + p_{total2}$$

The measurable differential pressure is reduced more pronouncedly with increasing flow speed, as a result of which the characteristic flattens. Small flows produce only a small effect; larger flows produce a correspondingly larger effect.

In the case of a known cross section of the flow channel, the volumetric flow rate can be deduced, and the latter can be controlled according to the requirements, on the basis of the difference between the overall pressures at the measurement outputs, said overall pressures being composed of static and dynamic pressure components in each case.

On account of the respective superposition of dynamic and static pressure in a differential pressure measurement path embodied according to the invention, the differential pressure exhibits an improved characteristic in view of the resolvability at low volumetric flow rates in comparison with a conventional differential pressure measurement path with a simple stop or a simple resistor, said improved characteristic approximating the characteristic of the system, i.e., the combination of the characteristics of measurement path and pressure sensor(s), to a linear characteristic.

In advantageous embodiments of the invention, system characteristics are realizable between a linear characteristic, corresponding to a curve of $a \cdot x^1 + b$, and a characteristic with a curve corresponding to $a \cdot x^{1.5} + b$. In a particularly advantageous embodiment, a characteristic with a curve between $a \cdot x^1 + b$ and approximately $a \cdot x^{1.3} + b$ is realizable. Depending on the employed pressure sensor, the coefficient b can be approximately equal to 0.

Consequently, the improvement according to the invention in the transfer characteristic of the differential pressure measuring apparatus is realized by adapting the volumetric flow rate/differential pressure characteristic of the differential pressure measurement path.

Furthermore, in an advantageous embodiment, the ventilation method according to the invention is characterized in that the volumetric flow rate of the respiratory gas is determined with the aid of a differential pressure measuring apparatus, the latter having a differential pressure measurement path, in which a respiratory gas volumetric flow rate dependent differential pressure is produced, and having a differential pressure sensor that captures the differential pressure and converts the latter into an electronic variable, and in that the volumetric flow rate of the respiratory gas present is determined with the aid of a microcontroller from the electronic variable produced by the differential pressure sensor.

Moreover, in a particularly advantageous embodiment, the ventilation method according to the invention is characterized in that the differential pressure measurement path employed to determine the volumetric flow rate of the respiratory gas has measurement nozzles that are flanged onto the flow channel in such a way that the alignment of the measurement lines, at least in the region of the measurement openings, has an essential component that is tangential to the outer delimiting face of the flow channel and/or to the principal flow direction of the respiratory gas in the flow channel.

BRIEF DESCRIPTION OF THE DRAWING

Various exemplary embodiments and configurations of the invention are imaged in the figures below. In detail.

DETAILED DESCRIPTION OF THE INVENTION

Figure 1:
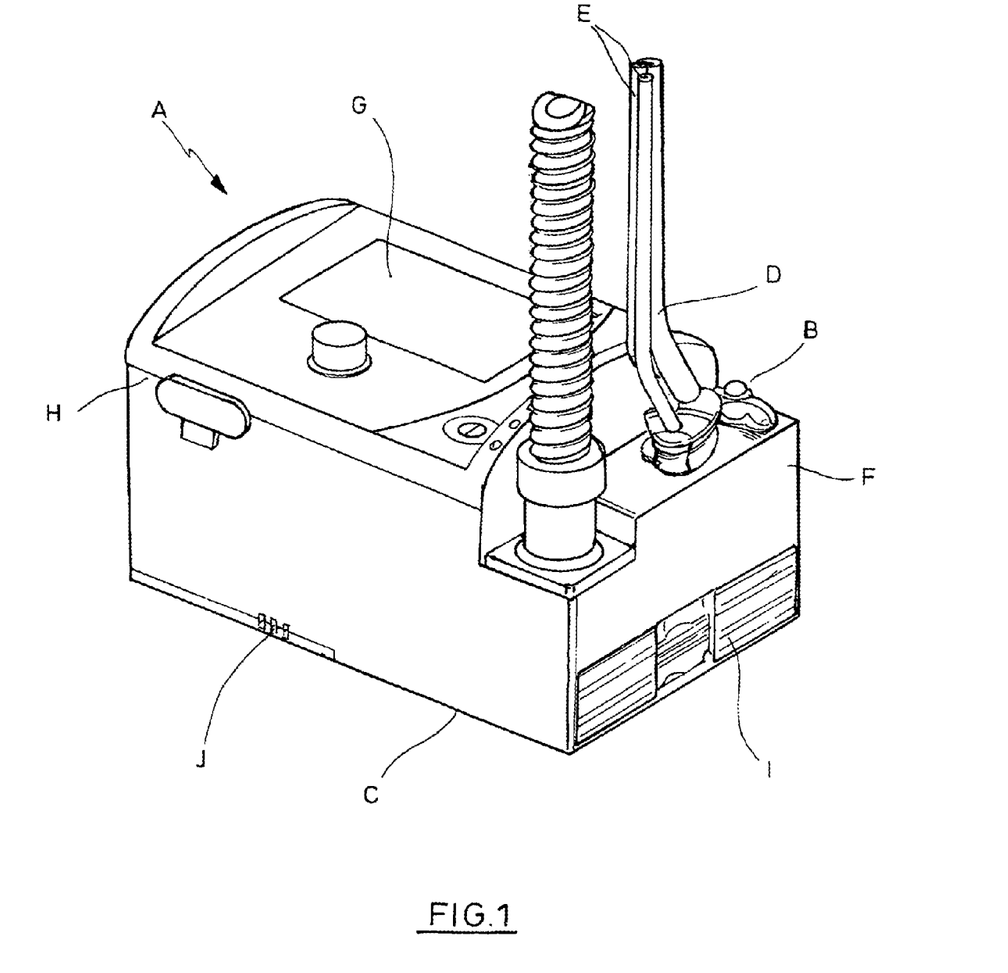
FIG. 1: shows a perspective illustration of a ventilator according to the invention.

FIG. 1 shows a perspective illustration of a ventilator apparatus (A) according to the invention, comprising a pressure connector (B) for connection to an oxygen source, a connector for a ventilation tube (C), by means of which the respiratory gas is guidable to a ventilation mask, and a combined connector for an oxygen tube (D) and a measuring tube system (E), embodied as a pressure measuring tube and a PEEP control tube. Furthermore, the ventilator apparatus (A) comprises an accessories connector (F), a display (G), an operating element (H) embodied as a rotary knob and an air inlet (I) and air outlet (J).

Figure 2:
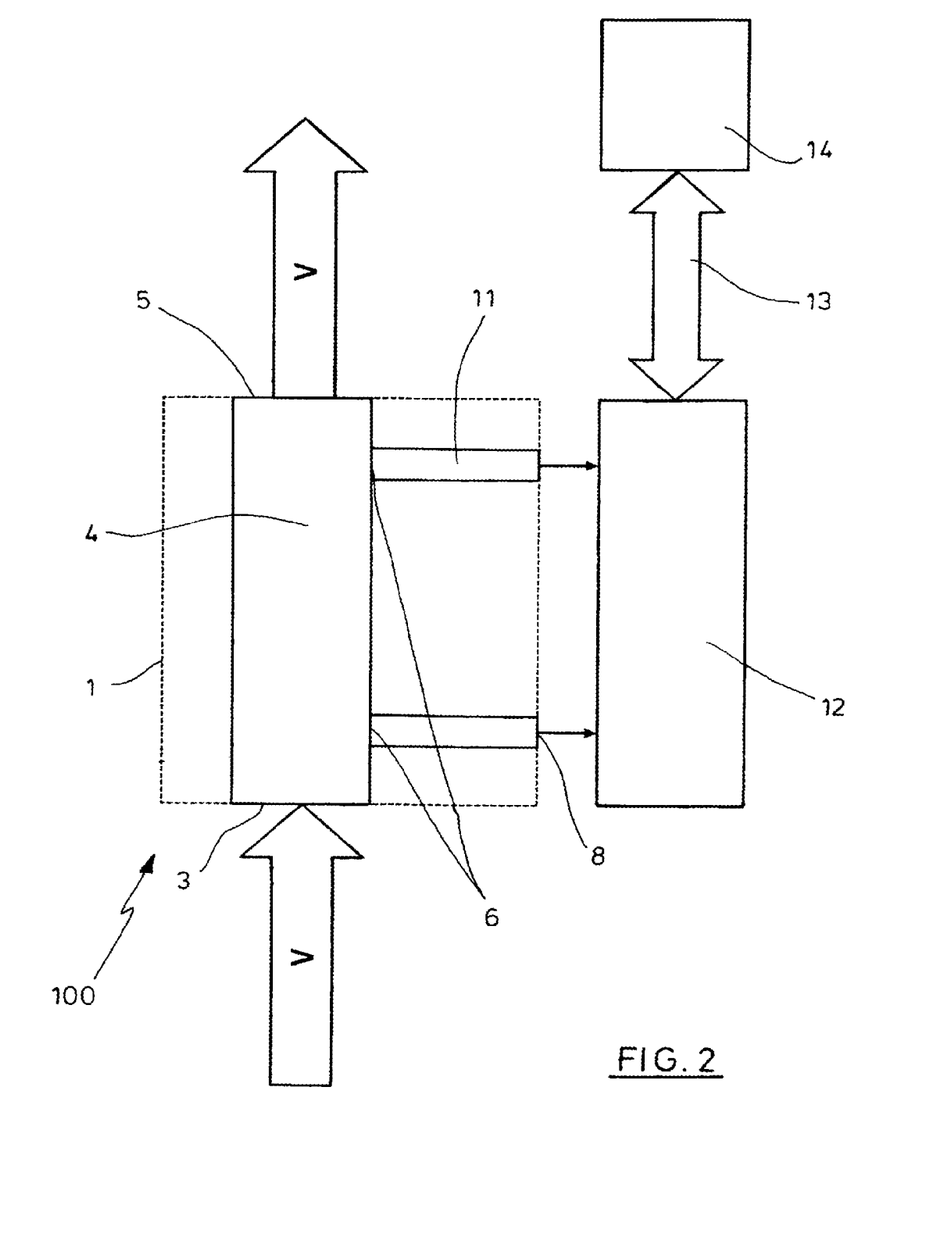
FIG. 2: shows a block diagram of a differential pressure measuring apparatus, according to the invention, of a ventilator.

FIG. 2 illustrates a sectional block diagram of an embodiment of a ventilator apparatus (A) according to the invention. The section shown relates to the differential pressure measuring apparatus (100) of the ventilator apparatus (A) according to the invention. A respiratory gas at a volumetric flow rate (V) flows into a differential pressure measurement path (1) having a flow channel (4) via an inflow opening (3) and flows out of said flow channel via an outflow opening (5) at the end of the flow channel (4). The volumetric flow rate (V) produces local pressures in the differential pressure measurement path (1), which are applied by way of two measurement openings (6) at an assigned measurement output (8) via a measurement line (11) in each case. A differential pressure sensor (12), which captures the pressures and, moreover, digitizes these in the illustrated exemplary embodiment, is connected to the measurement outputs (8). The pressure measurement data are readable from the differential pressure sensor (12) with the aid of a microcontroller (14) via an interface (13), which is realized as an I2C interface. On the basis of the system parameters and with the aid of the microcontroller (14), the volumetric flow rate (V) of the respiratory gas is determinable, and usable for closed-loop control, from the digital pressure measurement data.

Figure 3:
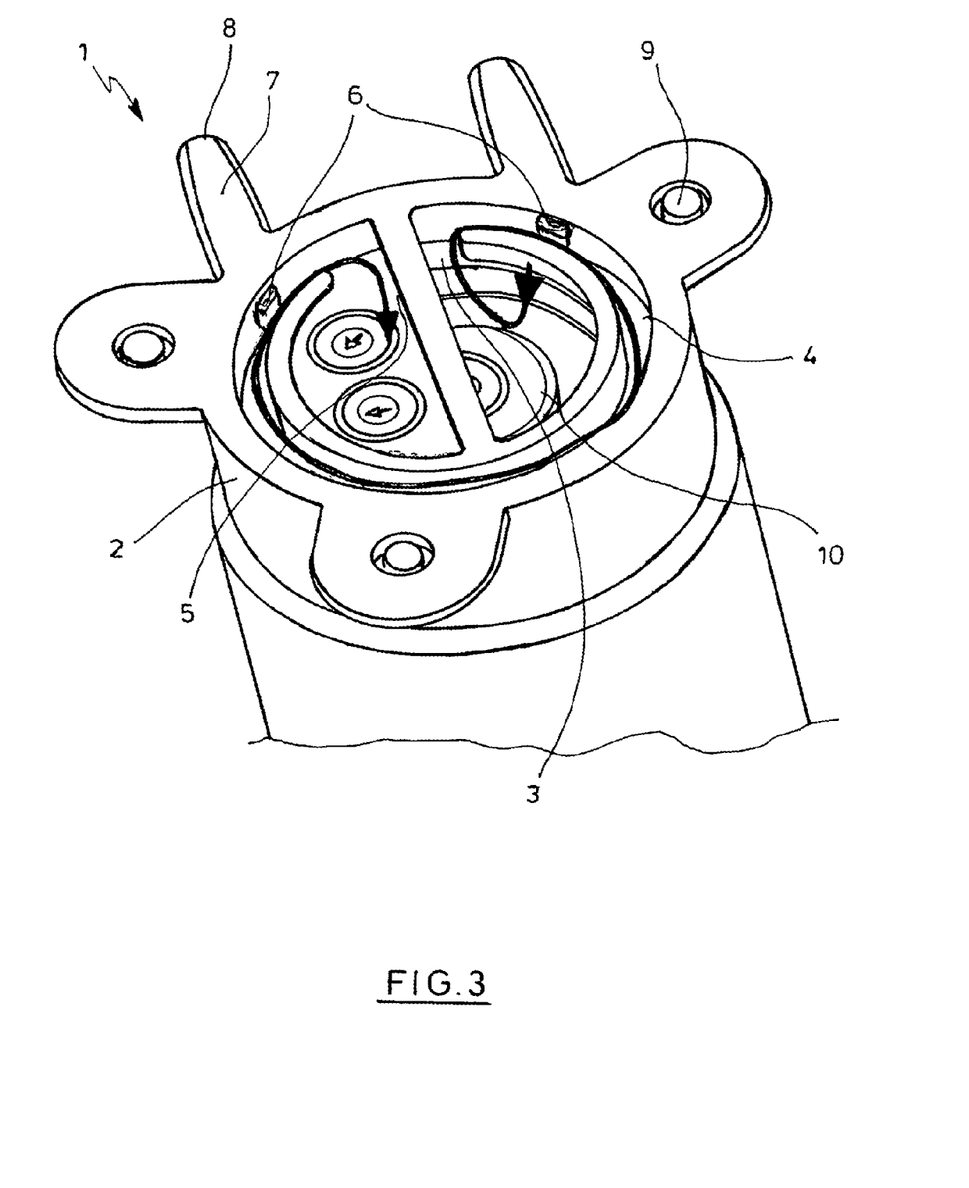
FIG. 3: shows a perspective illustration of a differential pressure measurement path embodied according to the invention, integrated into an adapter.

FIG. 3 shows a perspective illustration of a section of an embodiment according to the invention of a differential pressure measurement path (1), which is integrated into an adapter (2). The differential pressure measurement path (1) has a circular segment-shaped inflow opening (3), through which a respiratory gas flows into the differential pressure measurement path (1) at a pressure and/or volumetric flow rate (V) that is regulated by the ventilator apparatus (A). The respiratory gas is guided away from the inflow opening (3) through a flow channel (4), which has a ring segment-like embodiment and a rectangular cross section. At its upper side, the flow channel (4) is delimited and sealed by a cover that is not illustrated here. At its other end, the flow channel (4) has an outflow opening (5), through which the respiratory gas escapes from the flow channel (4).

In particular, a rectangular, square or circular cross section of the flow channel (4) is considered since the properties of the flow are known for channels with such an embodiment and the cross section is easy to calculate. However, other cross sections for a flow channel (4) for a differential pressure measurement path (1) of a ventilator apparatus (A) according to the invention are also conceivable.

Two measurement openings (6) are arranged on the radially outer delimiting face of the flow channel (4). The measurement openings (6) are adjoined by pressure measurement nozzles (7), which are arranged with an essential tangential directional component in relation to the local principal flow direction of the respiratory gas. At the other end, the pressure measurement nozzles (7) each have a measurement output (8), to which a pressure measuring unit is couplable. Three fastening apparatuses (9) are arranged radially on the outside of the adapter (2) that integrates the differential pressure measurement path (1), said fastening apparatuses being embodied as a screw thread and serving for a secure attachment of the adapter (2) within the ventilator apparatus (A).

Furthermore, a sprung positive pressure valve (10) is arranged in the region of the inflow opening (3) of the differential pressure measurement path (1), said positive pressure valve opening in the case of positive pressure in the respiratory gas line and reducing the pressure.

Figure 4:
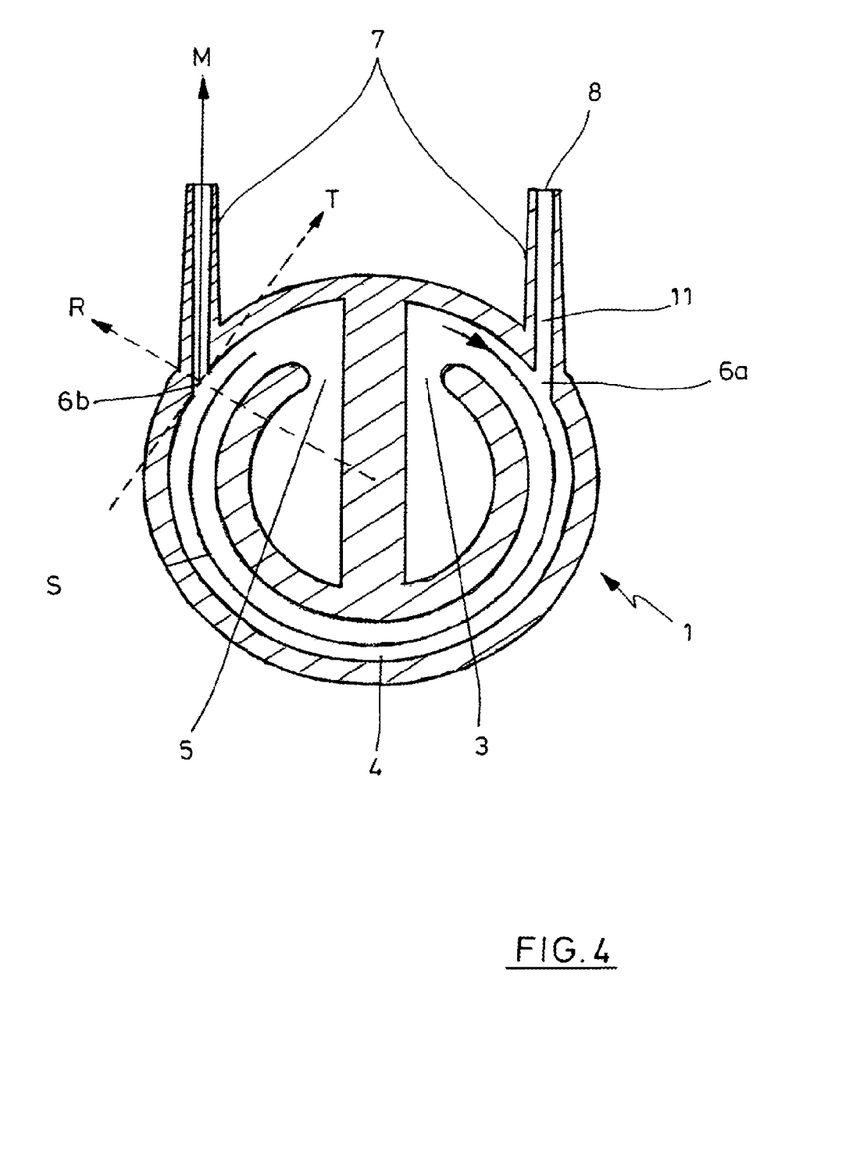
FIG. 4: shows a plan view of a section through the adapter in the region of the differential pressure measurement path

FIG. 4 illustrates a section of the differential pressure measurement path (1). The flow channel (4) is delimited on the radial inner and outer side by the material of the adapter (2) in a ring segment-like contour. A particularly compact structure of the differential pressure measurement path (1) is realized by the ring-like embodiment of the flow channel (4). Moreover, the illustrated arrangement of the pressure measurement nozzles (7) or of the measurement lines (11) within the pressure measurement nozzles (7) is particularly advantageously realizable with an essential directional component tangential to the local principal flow direction (S) of the respiratory gas or to the local outer delimiting face of the flow channel (4) in the region of the measurement opening (6).

A locally (in the region of the measurement opening) tangentially aligned axis (T) spans a plane with a locally radially aligned axis (R), in which plane the alignment (M) of a measurement line (11) lies in a range from 0° to 60° about the tangentially aligned axis (T).

Within the flow channel (4) with the ring segment-like embodiment, the local principal flow direction (S) of the respiratory gas is substantially tangential to the circular form of the radially outer channel boundary. If the measurement lines (11) are arranged with an essential directional component (M) in this tangential direction T, at least in the region of the measurement openings (6), this, according to the invention, influences the volumetric flow rate/differential pressure characteristic of the differential pressure measurement path (1) in such a way that the volumetric flow rate/differential pressure characteristic of the differential pressure measuring apparatus approaches a linear characteristic from the direction of the known quadratic dependence of the characteristic.

Figure 5:
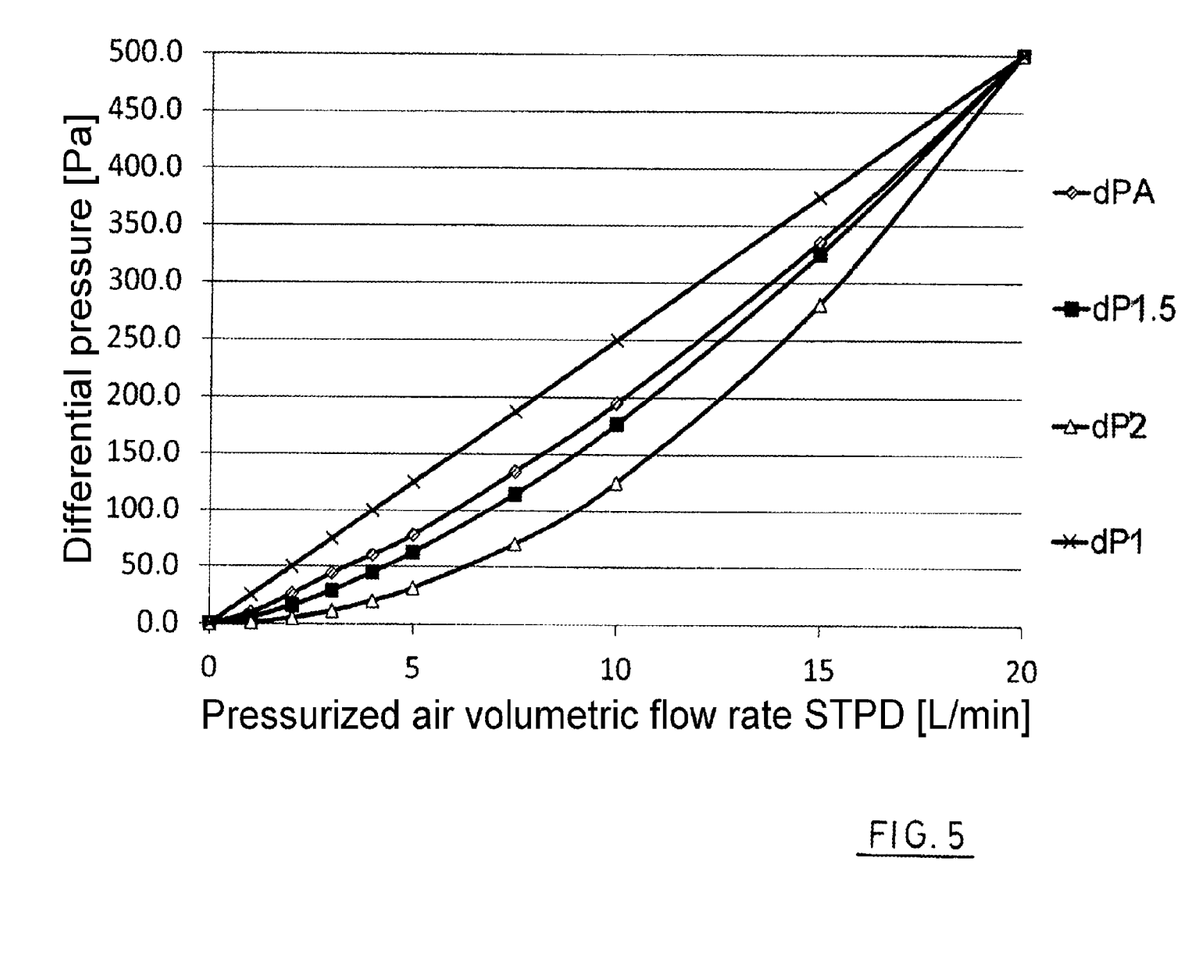
FIG. 5: shows a typical characteristic curve for a volumetric flow rate measurement.

FIG. 5 shows a diagram with different volumetric flow rate/differential pressure characteristics, which each represent the system characteristic by way of the differential pressure measurement path and pressure sensors. In this illustration, a sought-after volumetric flow rate measurement range of 20 L/min STPD (standard temperature and pressure dry) is set and a maximum measurement range of 500 Pa is given by the employed differential pressure sensor.

For an ideal resolvability, the differential pressure increases linearly (dP1). In this case, the differential pressures are already sufficiently high in the lower volumetric flow rate range in order to be well resolvable.

In the case of a conventional differential pressure measurement path (simple stop or simple resistor), a behavior of the differential pressure proportional to the square of the volumetric flow rate (dP2) is typically exhibited. In this case, the differential pressure measurement values are very small in the lower volumetric flow rate range.

The structure according to the invention described here facilitates, by way of a simple design, a characteristic (differential pressure versus volumetric flow rate) in which the differential pressure is approximately proportional to the 1.5-th power of the volumetric flow rate (dP1.5).

A pressure measurement using a differential pressure measuring apparatus according to the invention exhibited a volumetric flow rate/differential pressure characteristic that was proportional to the 1.3-th power (dPA).

The invention claimed is:

1. A ventilator apparatus, comprising: at least one differential pressure measurement path; and a differential pressure sensor, wherein the differential pressure measurement path has a flow channel with at least two measurement openings that are arranged between an inflow opening and an outflow opening of the flow channel and are joined by measurement lines arranged in measurement nozzles, wherein a respiratory gas is guided from the inflow opening to the outflow opening through the flow channel in a principal flow direction, wherein a volumetric flow rate/differential pressure characteristic curve is realized by the differential pressure measurement path in conjunction with the differential pressure sensor, said characteristic curve lying between a linear curve $a \cdot X^{1.0}+b$ and a curve describable by $a \cdot X^{1.5}+b$, wherein b is approximately equal to 0, wherein, in the principal flow direction of the respiratory gas through the flow channel, the flow channel is at least partly ring-shaped or is a ring segment, wherein the measurement nozzles are flanged onto the flow channel so that an alignment of the measurement lines, at least in a region of the measurement openings, has a component that is tangential to an outer delimiting face of the flow channel and/or to the principal flow direction of the respiratory gas in the flow channel, and wherein the alignment of one of the measurement lines, at least in the region of the measurement openings, lies in an angular range of 0° to 60° about an axis defined by a local tangent in a direction of an axis that is orthogonal to the local tangent and extends in a radial direction, wherein the flow channel is arranged in an adapter that connects the ventilator apparatus with a respiration tube, and wherein the flow channel is limited in a radial inward direction and a radial outward direction by a material of the adapter.

2. The apparatus according to claim 1, wherein, given the principal flow direction of a respiratory gas through the flow channel of the differential pressure measurement path, a static pressure and a dynamic, volume flow dependent negative pressure are present in the region of a first of the measurement openings and a static pressure and a dynamic, volume flow dependent positive pressure are present in the region of a second of the measurement openings.

3. The apparatus according to claim 1, wherein the alignment of the measurement lines, in the region of the measurement openings, is realized approximately counter to the principal flow direction for the first measurement opening and approximately in the direction of the principal flow direction for the second measurement opening.

4. The apparatus according to claim 1, wherein the apparatus is an emergency ventilator.

5. The apparatus according to claim 4, wherein the apparatus is a mobile emergency ventilator.

* * * * *